United States Patent
Neumann

(10) Patent No.: US 11,942,214 B2
(45) Date of Patent: Mar. 26, 2024

(54) METHOD FOR AND SYSTEM FOR GENERATING AN OBJECT PRIORITIZATION LIST FOR PHYSICAL TRANSFER

(71) Applicant: KPN INNOVATIONS, LLC., Lakewood, CO (US)

(72) Inventor: Kenneth Neumann, Lakewood, CO (US)

(73) Assignee: KPN Innovations, LLC, Lakewood, CO (US)

(*) Notice: Subject to any disclaimer, the term of this patent is extended or adjusted under 35 U.S.C. 154(b) by 0 days.

(21) Appl. No.: 17/087,753

(22) Filed: Nov. 3, 2020

(65) Prior Publication Data
US 2022/0139534 A1    May 5, 2022

(51) Int. Cl.
| | |
|---|---|
| *G16H 40/20* | (2018.01) |
| *A61B 5/00* | (2006.01) |
| *G16H 10/60* | (2018.01) |
| *G16H 50/20* | (2018.01) |
| *G16H 50/30* | (2018.01) |
| *G16H 50/70* | (2018.01) |

(52) U.S. Cl.
CPC ........... *G16H 40/20* (2018.01); *A61B 5/7267* (2013.01); *G16H 10/60* (2018.01); *G16H 50/20* (2018.01); *G16H 50/30* (2018.01); *G16H 50/70* (2018.01)

(58) Field of Classification Search
CPC ........ G16H 10/60; G16H 40/20; G16H 50/20; G16H 50/30; G16H 50/70; A61B 5/7267
See application file for complete search history.

(56) References Cited

U.S. PATENT DOCUMENTS

| | | | | |
|---|---|---|---|---|
| 10,360,616 | B2* | 7/2019 | Lopez | G06Q 30/0635 |
| 2010/0161353 | A1* | 6/2010 | Mayaud | G16H 10/60 705/3 |
| 2014/0244279 | A1* | 8/2014 | Bezdek | G06Q 30/0283 705/2 |
| 2014/0324457 | A1* | 10/2014 | Kim | G16H 50/20 705/3 |
| 2019/0163875 | A1* | 5/2019 | Allen | G16H 50/70 |
| 2019/0392935 | A1* | 12/2019 | Breese | G07F 9/026 |
| 2020/0027554 | A1* | 1/2020 | Boroczky | G16H 30/40 |
| 2020/0097900 | A1* | 3/2020 | Kibbey | G06F 16/212 |
| 2020/0143946 | A1* | 5/2020 | Lewis | G16H 10/60 |
| 2020/0349509 | A1* | 11/2020 | Sharma | G06Q 10/047 |
| 2020/0381107 | A1* | 12/2020 | Lowry | G16H 40/20 |

\* cited by examiner

*Primary Examiner* — Fonya M Long
*Assistant Examiner* — Anthony Balaj
(74) *Attorney, Agent, or Firm* — Caldwell Intellectual Property Law

(57) ABSTRACT

A system for generating an object prioritization list for physical transfer, the system comprising a computing device configured to receive a biological extraction of a user, determine, using the biological extraction, a plurality of urgency metrics, wherein determining the plurality of urgency metrics including training an urgency machine-learning model with training data that includes a plurality of entries wherein each entry correlates biological extraction data to metrics of urgency of object-addressable maladies, and determining the plurality of urgency metrics as a function of the urgency machine-learning model, order, using a first ranking machine-learning process, a plurality of candidate objects as a function of the plurality of urgency metrics, and generate an object prioritization list as a function of the ordered plurality of candidate objects.

16 Claims, 6 Drawing Sheets

METHOD FOR AND SYSTEM FOR GENERATING AN OBJECT PRIORITIZATION LIST FOR PHYSICAL TRANSFER

FIELD OF THE INVENTION

The present invention generally relates to the field of machine-learning. In particular, the present invention is directed to systems and methods for generating an object prioritization list for physical transfer.

BACKGROUND

In addition to providing a physical and virtual space for objects at a physical location, providers may also physically transfer such objects to users. As a result, systems configured for physically transferring objects to users may result in a poor user experience; especially if the user experience is directed to metrics that indicate that the user is somehow better than others, or that they should be favored and/or receive superior service over others as a function of purchasing power or habits.

SUMMARY OF THE DISCLOSURE

In an aspect, a system for generating an object prioritization list for physical transfer, the system comprising a computing device configured to receive a biological extraction of a user, determine, using the biological extraction, a plurality of urgency metrics, wherein determining the plurality of urgency metrics including training an urgency machine-learning model with training data that includes a plurality of entries wherein each entry correlates biological extraction data to metrics of urgency of object-addressable maladies, and determining the plurality of urgency metrics as a function of the urgency machine-learning model, order, using a first ranking machine-learning process, a plurality of candidate objects as a function of the plurality of urgency metrics, and generate an object prioritization list as a function of the ordered plurality of candidate objects.

In another aspect, a method for generating an object prioritization list for physical transfer, the method comprising receiving, by a computing device, a biological extraction of a user, determining, by the computing device, using the biological extraction, a plurality of urgency metrics, wherein determining the plurality of urgency metrics includes training an urgency machine-learning model with training data that includes a plurality of entries wherein each entry correlates biological extraction data to metrics of urgency of object-addressable maladies, and determining the plurality of urgency metrics as a function of the urgency machine-learning model, ordering, by the computing device, using a first ranking machine-learning process, a plurality of candidate objects as a function of the plurality of urgency metrics, and generating, by the computing device, an object prioritization list as a function of the ordered plurality of candidate objects.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating an object prioritization for physical transfer. In an embodiment, system comprises a computing device configured to receive a biological extraction of a user and train a machine-learning model to generate urgency metrics relating to object-addressable maladies of the user. Computing device may be configured to use machine-learning to determine an urgency metric, utility metric, and/or reliability metric, in generating an object prioritization for a plurality of objects for physical transfer. In an embodiment, computing device may be configured to generate an objective function of the plurality of candidate object prioritizations to minimize the time of physical transfer as a function of prioritization and generate a prioritization queue based on the urgency of the maladies and importance of the objects in addressing the maladies.

Figure 1:
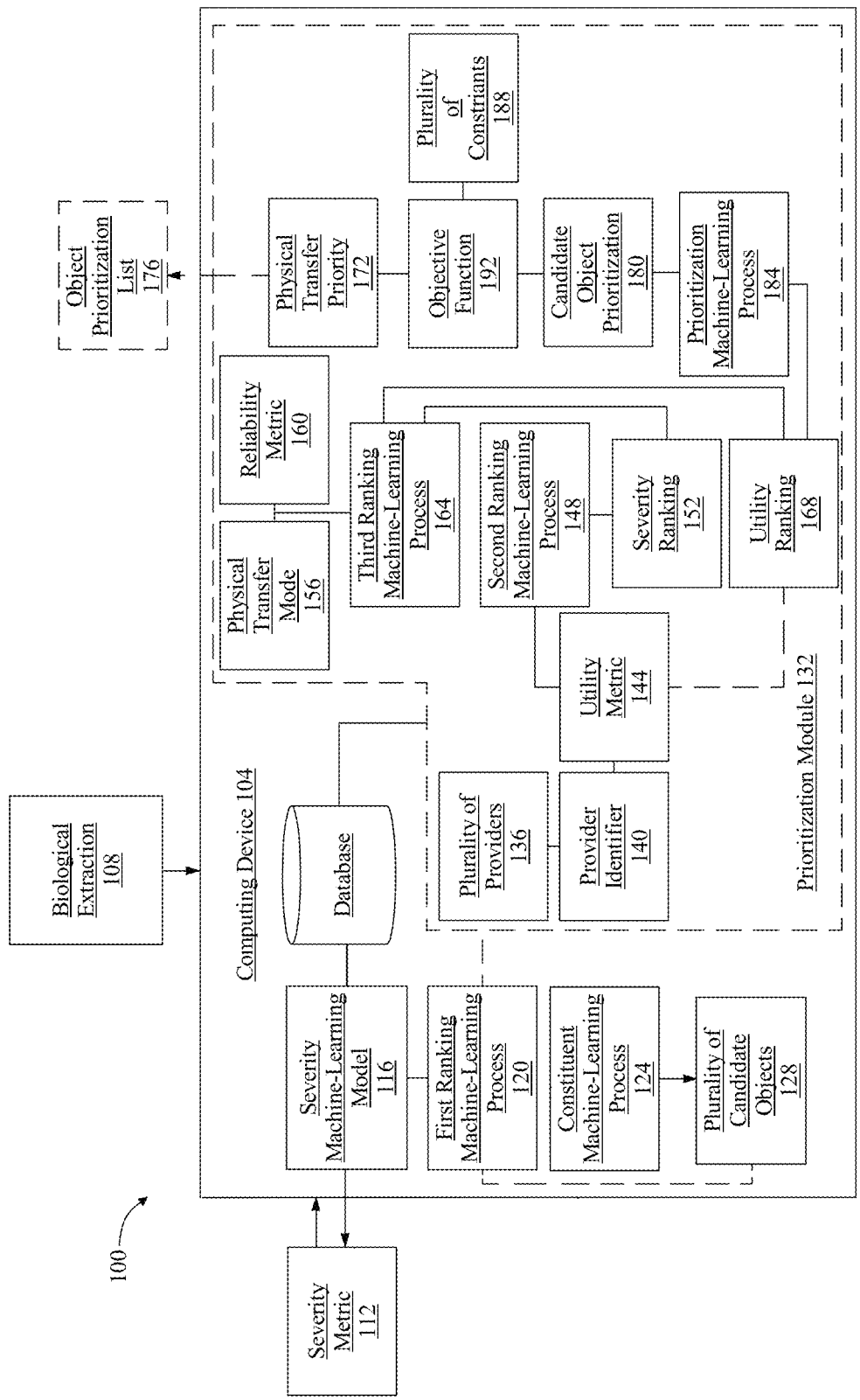
FIG. 1 is a block diagram illustrating an exemplary embodiment of a system for generating an object prioritization list for physical transfer.

Referring now to FIG. 1, an exemplary embodiment of a system 100 for generating an object prioritization for physical transfer is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Continuing in reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, "physical transfer," as used in this disclosure, is the process of physically obtaining an object for physically transferring the object to a physical site associated with a user. As used in this disclosure, "physical site" is a geophysical location, which may include an address, global positioning system (GPS) coordinates, latitude and longitude coordinates, and the like, associated with a user, provider, and/or object. Additionally, as used in this disclosure, "physical transfer path" is a geophysical path used for physically transferring an object.

Continuing in reference to FIG. 1, computing device 104 may be configured to receive a biological extraction of a user. A "biological extraction," as used in this disclosure, is an element of biological, chemical, physiological, medical, genetic, behavioral, and/or psychological data that is associated with a user, including past data, currently-generated data, and simulated and/or predicted future data. Biological extraction 108 data may include medical histories, diseases, surgeries, injuries, symptoms, exercise frequency, sleep patterns, lifestyle habits, and the like, that may be used to inform a user's lifestyle, including diet, and the like. Biological extraction 108 data may include diet information such as nutrition deficiencies, food intolerances, allergies, and the like. Biological extraction 108 may include data generated, collected, and/or transmitted by a wearable device such as accelerometer data, pedometer data, gyroscope data, electrocardiography (ECG) data, electrooculography (EOG) data, bioimpedance data, blood pressure and heart rate monitoring, oxygenation data, biosensors, fitness trackers, force monitors, motion sensors, audio-visual capture data, social media platform data, and the like. Biological extraction 108 data may be provided by a second individual on behalf of a user, for instance and without limitation a physician, medical professional, nurse, hospice care worker, mental health professional, and the like. Biological extraction 108 may alternatively or additionally include any data used as a biological extraction as described in U.S. Nonprovisional application Ser. No. 16/886,647, filed on May 28, 2020, and entitled "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, computing device 104 is configured to determine, using the biological extraction 108, a plurality of urgency metrics. A "urgency metric," as used in this disclosure, is a qualitative and/or quantitative determination of the physiological urgency of a malady present in a user's biological extraction 108 data. A malady may include diseases such as diabetes, cancer, neurodegeneration, high cholesterol, blood pressure, anemia, severe nutritional deficiencies, chronic and acute infections, and the like. A malady may include any biologically significant deviation from a threshold value of a healthy, or otherwise normal, individual. For instance and without limitation, a malady may include lifestyle maladies such as be sleep deprivation, nutrition deficiencies, poor exercise frequency, high blood pressure, hyperglycemia/hypoglycemia, excessive thirst, poor muscular endurance, low VO2 max, and the like, wherein determinations such as "deprivation", "deficiency," "poor", "high", "hyper", "hypo", "excessive", "low", among other determinations, may include determinations based on thresholds computing device 104 may search and/or locate for healthy, or otherwise normal, individuals and relate to the urgency. Computing device 104 may determine and assign a urgency metric 112 to a malady based on the magnitude of the malady, for instance and without limitation, if a malady represents an immediate and/or imminent reduction of quality-of-life, pain and discomfort, sharp reduction of life expectancy, terminal illness, or other high urgency determinations, versus a malady that represents a minor inconvenience, pain, discomfort, an acute malady, a chronic malady, a malady that represents a severe limitation to movement, utility, or difficulty to live versus maladies that represent minor limitations to a user's lifestyle. An urgency metric 112 may relate to a malady based upon how easily a malady may be addressed by an object, a user intervention, existing medical technologies, and the like. In such an instance, a user's biological extraction may include maladies of varying urgency, but the maladies are not addressable in any discernable way by user, may have a urgency metric assigned, but not an object, and thus may be filtered out or otherwise excluded for purposes described herein.

Continuing in reference to FIG. 1, determining the plurality of urgency metrics 112, using the biological extraction 108, includes training a urgency machine-learning model with training data that includes a plurality of entries wherein each entry relates user biological extraction to metrics of urgency correlated to object-addressable maladies. Training data may originate from the data present in a user's biological extraction, as described above, for instance user blood sugar as a function of time from medical history and user thirst experience from questionnaire data, wherein the training data may relate to blood sugar rates and perceived thirst by other users to train a model to recognize diabetes-like symptoms and a plurality of objects a diabetic may use as a function of the urgency of their symptoms. An alimentary machine-learning model 116 may be generated by a computing device 104 performing a machine-learning algorithm and/or process by using a machine-learning module, as described in further detail below. Training urgency machine-learning model 116 with training data may result in a model that contains a variety of qualitative and/or quantitative patterns, heuristics, or the like, that describe relationships between maladies described (wholly or in-part) in biological extraction 108 and urgency metrics, wherein the urgency is related to object-addressability of the maladies.

Still referring to FIG. 1, as used in this disclosure, "object-addressability" is a measure, assessment, and/or determination of how 'addressable' a malady may be according to objects that were located by computing device 104 and trained models. "Objects," as used in this disclosure include objects that can be used to address a malady, as described above, for instance objects used by patients (in-patient and/or out-patient), wearable devices, medical devices and diagnostic tools such as blood glucose and/or ketone monitor, syringes, medications, wheelchairs, crutches, joint wraps, neck supports, slings, nutrition supplements, alimentary elements such as meal kits, groceries, and the like, that may include objects user may obtain to address a malady. An "object-addressable malady," used in this disclosure, is a malady-object pairing determined by and/or located by computing device 104, as described herein. An object-addressable malady may include any malady-object pairing such as plantar fasciitis and therapeutic insoles for ameliorating the plantar fasciitis, wherein plantar fasciitis is an object-addressable malady in that computing device 104 may identify at least an object for addressing the plantar fasciitis.

Continuing in reference to FIG. 1, objects relating to an object-addressable malady for which an urgency metric 112 may be associated may include alimentary combinations, including supplements, meal kits, and the like. Urgency machine-learning model 116 may determine a user biological extraction indicates a nutritional deficiency, wherein the urgency of the nutritional deficiency may depend on the presence of symptoms, for instance and without limitation, dangerously low blood iron concentrations may manifest as gastrointestinal pain, lethargy, and minor hair loss, wherein the urgency metric 112 may indicate high urgency and a dire need for a user to obtain objects associated with increasing blood iron concentration, home iron testing strips, device, or the like. A plurality of urgency metrics 112 for object prioritization may be associated with nutrition deficiencies, alimentary combinations, and object ordering instructions, schedules, and the like, as described in U.S. Nonprovisional application Ser. No. 16/939,268, filed on Jul. 27, 2020, and entitled "SYSTEMS AND METHODS FOR SCHEDULING ALIMENTARY COMBINATIONS," the entirety of which is incorporated herein by reference.

Continuing in reference to FIG. 1, objects relating to an object-addressable malady for which an urgency metric 112 may be associated may include wearable devices, as described above. Urgency machine-learning model 116 may determine a user biological extraction indicates a co-morbidity associated with heart rate during exertion, such as exercise, climbing stairs, running errands, stressful situations, wherein the urgency of the co-morbidity may depend on the presence of symptoms, for instance and without limitation, dangerously high heart rate and blood pressure may manifest as throbbing sensation, bloody nose, and trouble sleeping, wherein the urgency metric 112 may indicate high-to-moderate urgency and for a user to obtain objects associated with controlling heart rate and blood pressure, including wearable devices for tracking athletic performance, health risk, blood pressure, force, heart rate, or the like.

Continuing in reference to FIG. 1, computing device 104 is configured to determine the plurality of urgency metrics 112 as a function of the urgency machine-learning model 116. Computing device 104 may store and/or retrieve metrics and/or determinations described herein, such as urgency metrics 112, in a database as described in further detail below. Urgency machine-learning model 116 may output individual urgency metrics 112 for a variety of object-addressable maladies. Urgency machine-learning model 116 may 'learn' to output a plurality of urgency metrics 112, wherein metrics are grouped, combined, or otherwise added together, based on object-to-malady relationships in the model. For instance and without limitation, if a single object may be address multiple maladies, urgency metrics 112 associated with each object-to-malady relationship from the model may result in a single cumulative urgency metric 112 of the plurality of individual urgency metrics 112. Alternatively or additionally, in non-limiting illustrative examples, urgency machine-learning model 116 may generate an output that is a plurality of urgency metrics 112 for a single malady, wherein the single malady is addressable with multiple objects. In such an instance, each object may contain different, but congruent urgency metrics 112, or objects may be grouped, combined, or otherwise added together, so that all objects are included in a single urgency metric 112, the magnitude of which may be increased due to the amount of objects required.

Continuing in reference to FIG. 1, computing device 104 is configured to order, using a first ranking machine-learning process, a plurality of objects as a function of the plurality of urgency metrics. A first ranking machine-learning process may include any machine-learning algorithm and/or process performed by using a machine-learning module, as described in further detail below. First ranking machine-learning process 120 may accept an input that is a plurality of urgency metrics 112, wherein similarity metrics 112 may include associated plurality of objects and generate an output that is an ordered (ranked) list of the plurality of objects based on the urgency metrics. For instance and without limitation, first ranking machine-learning process 120 may order the urgency metrics in such a way that higher urgency corresponds to higher ordering. A first ranking machine-learning process 120 may order using a formula, equation, function, or the like, that considers urgency metrics 112 from comparing object prices, object quality, provider location, among other alimentary element metric categories. In non-limiting illustrative examples, first ranking machine-learning process 120 may order urgency metrics corresponding to the urgency of object-addressable maladies a user suffers, wherein the objects' ordering may correspond to their ability to address, treat, or otherwise ameliorate the maladies. In such an example, first ranking machine-learning process 120 may generate an output that is an ordering as a function of the urgency of a malady and the ability of an object to address said malady; for instance and without limitation, an object that treats an especially bad illness may receive a high ordering.

Continuing in reference to FIG. 1, ordering a plurality of objects as a function of the plurality of urgency metrics 112 may include identifying, using the plurality of urgency metrics 112 and a constituent machine-learning process, a plurality of objects for addressing the plurality of urgency metrics. Constituent machine-learning process may include any machine-learning algorithm and/or process performed by using a machine-learning module, as described in further detail below. Constituent machine-learning process 124 may accept an input of a plurality of urgency metrics 112 associated with a plurality of object-addressable maladies and generate an output of a plurality of objects for each object-addressable malady. Urgency machine-learning model 116 may generate urgency metrics 112 without an associated plurality of objects. Alternatively or additionally, urgency machine-learning model 116 may generate urgency metrics 112 with identifiers, labels, signifiers, or the like, that relate to searchable labels for locating a plurality of objects related to each urgency metric 112. In non-limiting illustrative examples, system 100 may include using a constituent machine-learning process 124 to search and/or retrieve a plurality of objects for addressing the plurality of maladies associated with the plurality of urgency metrics 112. In such a case, constituent machine-learning process 124 may accept an input of a plurality of ordered outputs generated by first ranking machine-learning process 120 and iteratively generate a plurality of candidate objects 128. Candidate objects 128 may include duplicate objects, objects that may supplant other objects, objects that a part of a series wherein a first object must be obtained prior to a second object, multiple objects in place where a single object may do, and the like.

Continuing in reference to FIG. 1, generating a plurality of candidate objects 128 may include using a classifying machine-learning process to generate a classifier. A classification machine-learning process may include any machine-learning algorithm and/or process performed by using a machine-learning module, as described in further detail below. A "classifier," as used in this disclosure, is configured to output at least a datum that labels or otherwise identifies a set of data that are clustered together, as described in further detail below. A classifier may represent a body of data that is a series of urgency metrics 112 from a plurality of users associated with candidate objects 128. In non-limiting illustrative examples, a classifier may relate to the prices of objects, availability of objects, efficacy of objects, user satisfaction of objects, and the like, that may be a packet of data used to search or otherwise identify a plurality of candidate objects 128.

Continuing in reference to FIG. 1, system 100 may include a prioritization module 132 operating on the computing device 104, the prioritization module designed and configured to receive the plurality of candidate objects for physical transfer to a physical site. A "prioritization module," as used herein is a computational module operating on the computing device 104 that is used for generating an object prioritization list of a plurality of candidate objects 128. Prioritization module 132 may initialize by receiving the plurality of candidate objects 128.

Continuing in reference to FIG. 1, prioritization module 132 may be configured to search and retrieve a plurality of providers for the plurality of candidate objects 128, wherein retrieving includes generating a plurality of provider identifiers for the plurality of providers. Prioritization module 132 may be configured to execute a machine-learning process, similar to a constituent machine-learning process, to use a plurality of candidate objects 128 as an input to search for and generate an output that is a plurality of providers. A "provider," as used in this disclosure, is an entity that would be responsible for storing, selling, and/or otherwise providing an object, including a manufacturer, supplier, department store, grocery store, health food store, convenience store, medical supplier, hospital, pharmacy, or the like. Prioritization module 132 may search for providers, for instance and without limitation, using text-based searches, SQL domain-specific searches, or any other suitable query method used by computing device 104, as described herein. For instance and without limitation, prioritization module 132 may use a web-based internet browser, online database, catalogue, or the like, to use the input of a plurality of candidate objects 128 to search for a plurality of providers 136, wherein each candidate object may have multiple associated providers, wherein providers may differ based on physical site, price, object availability, and the like. Prioritization module 132 may generate an output from the search that is a plurality of provider identifiers. A "provider identifier," as used in this disclosure, is an identifier that contains qualitative data (such as a 'yes' or 'no' that the provider matches an object, physical site, provider name, availability, etc.) and quantitative data (such as price, order limits, estimated times associated with an order, etc.). In non-limiting illustrative examples, a provider identifier 140 may include the name of a large chain nutrition supplement warehouse, a price associated with an object, the status of available of the object, and the address of the warehouse, and the cost of the warehouse to arrange physical transfer of object directly to user.

Continuing in reference to FIG. 1, prioritization module 132 may modify a list of a plurality of candidate objects 128 as a function of the plurality of provider identifiers 140. Prioritization module 132 may generate a file that is a list of candidate objects 128 that have associated provider identifiers 140, perhaps for instance and without limitation, eliminating or otherwise removing candidate objects 128 that prioritization module 132 was unable to locate data to generate a provider identifier, such as returning no provider identifications, physical locations, prices, and the like, which may be necessary for a user to obtain an object. The plurality of candidate objects 128 that are continued to be included in the list generated by the prioritization module 132 may be simply referred to herein as 'the plurality of objects'.

Continuing in reference to FIG. 1, prioritization module 132 may generate, using the plurality of provider identifiers 140, a plurality of utility metrics for the plurality of objects. Each provider identifier 140 may include a price associated with an object and a cost for the provider associated with providing the object. A "utility metric," as used in this disclosure is a metric that quantifies the value-cost tradeoff associated with the physical transfer of an object to a user.

For instance and without limitation, utility metric 144 may serve as a dual user-side and provider-side metric for determining the cost-value benefit of an object and expediting its physical transfer. In a non-limiting illustrative example, a first object may cost $2000 and an additional $200 to physically transfer to the user in comparison to a second object that may cost $50 and an additional $10 to physically transfer to the user may result in utility metrics 144 represented as ratios, such as 10:1 and 5:1, respectively. In such an example, the utility metric 144 for the two objects may indicate that the second object might be physically transfer to the user quicker due to the conferred cost-value benefit, wherein the user is paying 20% of the first object's total value in additional fees for obtaining the first object versus 10% of the second object's total value in additional fees for obtaining the second object. Alternatively or additionally, in further non-limiting illustrative examples, if the costs associated with the first object to accelerate physical transfer may be increased to $250 versus $15 to accelerate physical transfer of the second object, the second item may maintain priority, whereas $500 to accelerate physical transfer of the first object versus the original $10 physical transfer of the second object as the only option may switch priority from a utility metric 144 standpoint.

Continuing in reference to FIG. 1, prioritization module 132 may generate, using a second ranking machine-learning process, an urgency ordering of the plurality of objects as a function of the plurality of utility metrics 144 and the plurality of urgency metrics 112. Prioritization module 132 may use a second ranking machine-learning process 148 that is alike a first ranking machine-learning process 120, as described in further detail below, that executes a ranking function. A "urgency ordering," as used in this disclosure is a listing of an ordering of objects based the relationships between urgency metric 112 and utility metric 144. For instance and without limitation an urgency ordering 152 may coincidentally indicate a ranking of the 'urgency', or measure of biological importance to the user, and the 'utility' or measure worth of providing an object in a specified timeframe. Prioritization module 132 may accept an input that is an ordered plurality of candidate objects 128 and the associated plurality of provider identifiers 140, as described above, and may further accept as inputs the plurality of utility metrics 144, and the plurality of urgency metrics 112 associated with the candidate objects 128 to generate an output that is a urgency ordering 152 of the candidate objects 128 list. In non-limiting illustrative examples, system 100 may order the plurality of candidate objects 128 based on associated urgency metrics 112 and the prioritization module 132 may modify the ordering by generating an urgency ordering 152 as a function of utility metric 144. Likewise, for instance and without limitation, prioritization module 132 may output an ordering, via the plurality of utility metrics 144, that results in an object ordering increasing and/or decreasing according to a provider's ability to accommodate expedited physical transfer for an object.

Continuing in reference to FIG. 1, prioritization module 132 may search and retrieve a plurality of physical transfer modes for the plurality of objects, A "physical transfer mode," as used in this disclosure, is a method, process, and/or mode of physical transfer of an object. In non-limiting illustrative examples, physical transfer mode 156 may include the identity of an enterprise, including the type of physical transfer they use, that is associated with physical transfer of an object, wherein the enterprise is suitable for physical transfer of the object. For instance and without limitation, a physical transfer mode may be included with the costs associated with the object. Alternatively or additionally, a physical transfer mode may include the use of a separate, fee-driven enterprise that is equipped to physically transfer the object. In further non-limiting illustrative examples, a physical transfer mode 156 may differ depending on the object, for instance, a wheelchair may be physically transferred by a different physical transfer mode 144 than an alimentary element.

Continuing in reference to FIG. 1, prioritization module 132 may generate a plurality of reliability metrics for each combination of the plurality of physical transfer modes 144 with each of the plurality of objects. A "reliability metric," as used in this disclosure, is a metric that quantifies the qualitative and quantitative parameters associated with the physical site, physical transfer path, and physical transfer mode, associated with an object. A single object may have associated with it a plurality of reliability metrics 160 corresponding to the variety of processes, methods, and/or costs associated with the physical transfer of the object. For instance and without limitation, for an object being physically transfer from a long-distance provider, there may be a plurality of reliability metrics 160 associated with a variety of physical transfer modes, wherein each mode is a different fee-driven enterprise. In non-limiting illustrative examples, there may be an object that is physically transfer from within the same geophysical area as the user, wherein there may be a plurality of reliability metrics 160 associated with different physical transfer paths, wherein the physical transfer paths differ based on timeliness, potential for theft/loss, and the like. In further non-limiting illustrative examples, a plurality of reliability metrics 160 may be generated for a plurality of physical transfer modes 156 as a function of prioritization module 132 identifying if objects arrive intact versus damaged, how content the staff of the physical transfer mode 156 is, among other user reviews of the physical transfer mode. In such an example, a reliability metric 160 associated with a high-priority object may require a certain reliability threshold for selecting a physical transfer mode 156 because the object must arrive undamaged, immediately, and by a service that requires a signature to eliminate theft/loss.

Continuing in reference to FIG. 1, prioritization module 132 may generate a reliability metric 160 using a process like computing device 104 uses for generating an urgency metric 112. Prioritization module 132 may generate a reliability metric 160 by using, for instance and without limitation, a machine-learning model, wherein the machine-learning model is trained with training data. Training data may include a plurality of data entries wherein each data entry is a user review of a provider, for instance a numerical review such as a 1-5 rating of a plurality of physical transfer modes associated with physical transfer of a particular object. Training a machine-learning model with such training data may result in a model that accurately describes, or otherwise captures, the relationships between certain objects and their physical transfer modes 156. In non-limiting illustrative examples, such a model may illustrate that more expensive, high-priority, or otherwise critical objects, such as fragile electronic device, may be more reliably physically transferred by a particular physical transfer mode 156, provider, or the like. In such an example, an object prioritization list that reflects a reliability metric 160 pairing the most appropriate particle physical transfer mode 156 with an object may improve that object's priority, potentially suggesting a user execute ordering quickly.

In non-limiting illustrative examples, and further continuing in reference to FIG. 1, prioritization module 132 may generate a pattern of a plurality of reliability metrics 160 that indicate that an object, when physically transferred by a particular physical transfer mode 156 and to the zip code of the user physical site, has a 1-in-5 chance of arriving to the user damaged and/or stolen. In such a case, prioritization module may 'recognize,' for instance using a machine-learning process, such as a ranking machine-learning process as described herein, that object pairings with a physical transfer mode 156 that includes sign-only physical transfer and higher user satisfaction may decrease said chance to 1-in-20 of arriving damage and/or stolen. A reliability metric 160 reflecting said data may result in an object and physical transfer mode 156 pairing that may be ordered higher and added to a prioritization queue, as described in further detail below. However, in such examples, it is important to note that the physical transfer mode 156 requiring sign-only physical transfer may increase the costs of the physical transfer, in which case the utility metric 144 might change. In such an instance, an ordering may include both the utility metric 144 and the reliability metric 160 and adjust the ordering of objects according to any relationships between the two.

Continuing in reference to FIG. 1, prioritization module 132 may generate a utility ordering of the plurality of physical transfer modes as a function of the plurality of reliability metrics and the plurality of utility metrics. Prioritization module 132 may use a third ranking machine-learning process 164 like a first ranking machine-learning process 120, as described in further detail below, that executes a ranking function. A "utility ordering," as used in this disclosure, is a listing of an ordering of objects based the relationships between utility metric 112 and reliability metric 144. For instance and without limitation a utility ordering 168 may coincidentally indicate an ordering of the urgency ordering 152 of the objects as a function of the reliability metric 160 of the object, wherein the reliability metric 160 may change the ordering of an object from the ordering in the urgency ordering 152. Alternatively or additionally, a reliability metric 160 may indicate a physical transfer mode for an object that may alter an object's utility metric 144. In such an instance, prioritization module 132 may iteratively generate an updated utility metric 144, as described above, by inputting only the objects that are expected to have changed utility metrics 144. In such an instance, prioritization module 132 may iteratively generate a new urgency ordering 152 by including the new utility metric 144 paired with the object into the plurality of objects used for generating a first urgency ordering 152.

Continuing in reference to FIG. 1, prioritization module 132 may accept an input that is an urgency ordered plurality of objects and may further accept as inputs the plurality of reliability metrics 160 and generate an output that is a utility ordering 168. In non-limiting illustrative examples, system 100 may order the plurality of objects based on associated urgency orderings 152 and the prioritization module 132 may modify the urgency ordering 152 by generating a utility ordering 168 as a function of reliability metric 160. Likewise, for instance and without limitation, prioritization module 132 may output a utility ordering 168, using the plurality of reliability metrics 160, that results in an object ordering increasing and/or decreasing according to a physical transfer mode's ability to physically transfer an object reliably. Additionally, prioritization module 132 may output a utility ordering 168 that results in an altered object ordering depending on changes in utility metrics 144 from increasing reliability of a physical transfer mode.

Continuing in reference to FIG. 1, prioritization module 132 may be configured to generate an object prioritization list, wherein generating the object prioritization list includes using a prioritization machine-learning process to generate a plurality of candidate object prioritizations. A "candidate object prioritization," as used in this disclosure, contains a physical transfer priority for the plurality of objects and an object prioritization list for the physical transfer priority. A "physical transfer priority," is a prioritization ordering of physical transfer for a plurality of objects, wherein the priority is an ordering for the order of physical transfer as a function of the urgency metric 112, utility metric 144, and/or reliability metric 160 and the associated urgency ordering 152 and utility ordering 168. A physical transfer priority 172 may represent a finalized priority of objects for physical transfer based on the plurality of metrics and ordering steps described herein. An "object prioritization list," as used in this disclosure, is a list that contains instructions for prioritized physical transfer of all objects with their assigned physical transfer mode, indicated providers, timestamp for initiating ordering, and timestamp of expected arrival. In non-limiting illustrative examples, object prioritization list 176 is a list that specifies to system 100 and/or user in which order the objects should be delivered, ordered, including other information as described above. An object prioritization list 176 may include all instructions necessary for computing device 104 to initiate physical transfer of the plurality of objects, including the schedule of initiating the orders, the identity of the providers to place the orders, the physical transfer mode parameters to use, among other elements of data. Prioritization machine-learning process may generate an output that is a plurality of candidate object prioritizations 180, wherein the object prioritization that is the most 'optimal' or represents the 'best' solution may depend on a plurality of constraints, for instance and without limitation, timeframes when a user may participate in signing for an object, or if a physical transfer mode will be enable to physically transfer within the time frame required for an object, and the like.

Continuing in reference to FIG. 1, prioritization machine-learning process 184 may be generated by computing device 104 performing a machine-learning algorithm and/or process by using a machine-learning module, as described in further detail below. Prioritization machine-learning process 184 may accept an input that is a utility ordering 168 of a plurality of objects and generate a first output that is a physical transfer priority 172, which lists the plurality of objects in a prioritized ordering based on when each physical transfer process should commence for the plurality of objects to arrive in an order most closely resembling the utility ordering 168. In non-limiting illustrative examples, this may include initiating physical transfer protocols for a plurality of objects concurrently and/or in an order that deviates from the utility ordering 168. Prioritization machine-learning model may then accept an input that is the first output (physical transfer priority 172) and generate a second output that is an object prioritization list 176. Prioritization machine-learning process 184 may determine how to rank, or otherwise position, the plurality of objects for physical transfer as a function of their physical transfer priority 172 by recognizing instances such as the above, wherein initializing physical transfer process may alter priority. In doing so, prioritization machine-learning process 184 may generate a plurality of candidate object prioritizations 180, wherein a candidate object prioritization 180 is generated for each instance.

Continuing in reference to FIG. 1, generating the object prioritization list 176 using a prioritization machine-learning process 184 may include generating an objective function of the plurality of candidate object prioritizations 180 as a function of a plurality of constraints, wherein minimizing the objective function minimizes the time of physical transfer of the plurality of objects as a function of object priority. A "plurality of constraints," as used in this disclosure, is a physical and/or non-physical constraint placed on the order and/or delivery of a plurality of objects. A plurality of constraints 188 may include physical constraints such as tangible object-oriented constraints on ordering and/or physical transfer of objects. A plurality of constraints 188 may include non-physical constraints such as time constraints. A plurality of constraints 188 may include user-originated constraint, provider-originated constrain, and/or physical transfer mode-originated constraint on physical transfer of an object. For instance and without limitation, a plurality of constraints 188 may include user-indicated time restrictions for signing for an object, wherein the user is only available between 9:00 am and 12:00 pm on Monday, Wednesday, and Friday. In non-limiting illustrative examples, a constraint that may alter physical transfer mode and expected physical transfer time may include a first provider suddenly out-of-stock of an object, wherein the provider may require being switched to a second provider, which may in turn change the physical transfer mode, expected arrival, and/or reliability metric 160.

Continuing in reference to FIG. 1, computing device 104 may compute a score associated with a priority and/or ordering associated with each candidate object prioritization 180 and select variables associated with the candidate object prioritization, as described herein, to minimize and/or maximize the score depending on whether an 'optimal' or sufficiently 'good' solution is represented, respectively, by a minimal and/or maximal score; a mathematical function, described herein as an "objective function," may be used by computing device 104 to score each possible pairing of variables, wherein variables include physical transfer mode 156, physical transfer priority 172, and the like, given the plurality of constraints 188. Objective function 192 may be based on one or more objectives, as described in further detail below. For instance and without limitation, computing device 104 may pair an object, with a given physical transfer mode 156, that optimizes the objective function. In various embodiments, a score of a particular candidate object prioritization 180 may be based on a combination of one or more factors, as described herein. Each factor may be assigned a score based on predetermined variables. In some embodiments, the assigned scores may be weighted or unweighted.

Continuing in reference to FIG. 1, as used herein, "minimizing the objective function," is minimizing a difference from a goal representing a 'best' solution, where the goal could be a maximal output, minimal output, or target number/set of numbers. 'Optimizing' an objective function may include minimizing the time for physical transfer, physically transferring the plurality of objects in an order that most closely resembles the determined utility ordering 168, and the like. Alternatively or additionally, minimizing the physical resources used may refer to optimizing an objective function to achieve a maximal score, such as a maximal score in pairing an object with a provider with a physical transfer mode, wherein each pairing between increases reliability metric 160.

With continued reference to FIG. 1, minimizing the objective function 192 may include performing a greedy algorithm process. A "greedy algorithm" is defined as an algorithm that selects locally optimal choices, which may or may not generate a globally optimal solution. For instance, computing device 104 may select physical transfer modes 156 so that scores associated therewith are the best score for each physical transfer path and/or for each provider and/or each object. In such an example, optimization of a greedy algorithm may determine the combination of each such that pairing includes the highest score possible but may not represent a globally optimal solution for the entire object prioritization.

Still referring to FIG. 1, objective function 192 may be formulated as a linear objective function, which computing device 104 may solve using a linear program such as without limitation a mixed-integer program. A "linear program," as used in this disclosure, is a program that optimizes a linear objective function, given at least a constraint. For instance, the availability of physical transfer modes 156, the geophysical location of providers, availability of user, among other constraints. In various embodiments, system 100 may determine an object prioritization that maximizes a total score subject to a constraint, as described above. A mathematical solver may be implemented to solve for the set of candidate object prioritizations 180 that maximizes scores; mathematical solver may implement on computing device 104 and/or another device in system 100, and/or may be implemented on third-party solver.

With continued reference to FIG. 1, optimizing objective function may include minimizing a loss function, where a "loss function" is an expression of an output in which an optimization algorithm minimizes to generate an optimal result. As a non-limiting example, computing device 104 may assign variables relating to a set of parameters, which may correspond to score components as described above, calculate an output of mathematical expression using the variables, and selects an object prioritization that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs.

Continuing in reference to FIG. 1, objective function may be implemented as described above, and/or as described in U.S. Nonprovisional application Ser. No. 16/890,839, filed on Jun. 2, 2020, and entitled "METHODS AND SYSTEMS FOR PATH SELECTION USING VEHICLE ROUTE GUIDANCE," the entirety of which is incorporated herein by reference.

Continuing in reference to FIG. 1, computing device 104 may select the object prioritization list 176 that minimizes the time of physical transfer of the plurality of objects as a function of object priority. Computing device 104 may select the 'best' object prioritization list 176 output by objective function 192, as described above. In non-limiting illustrative examples, depending on the plurality of constraints 188, the object prioritization list 176 that is associated with the best solution may include an object priority that most closely resembles the utility ordering 168, urgency ordering 152, and the like.

Figure 2:
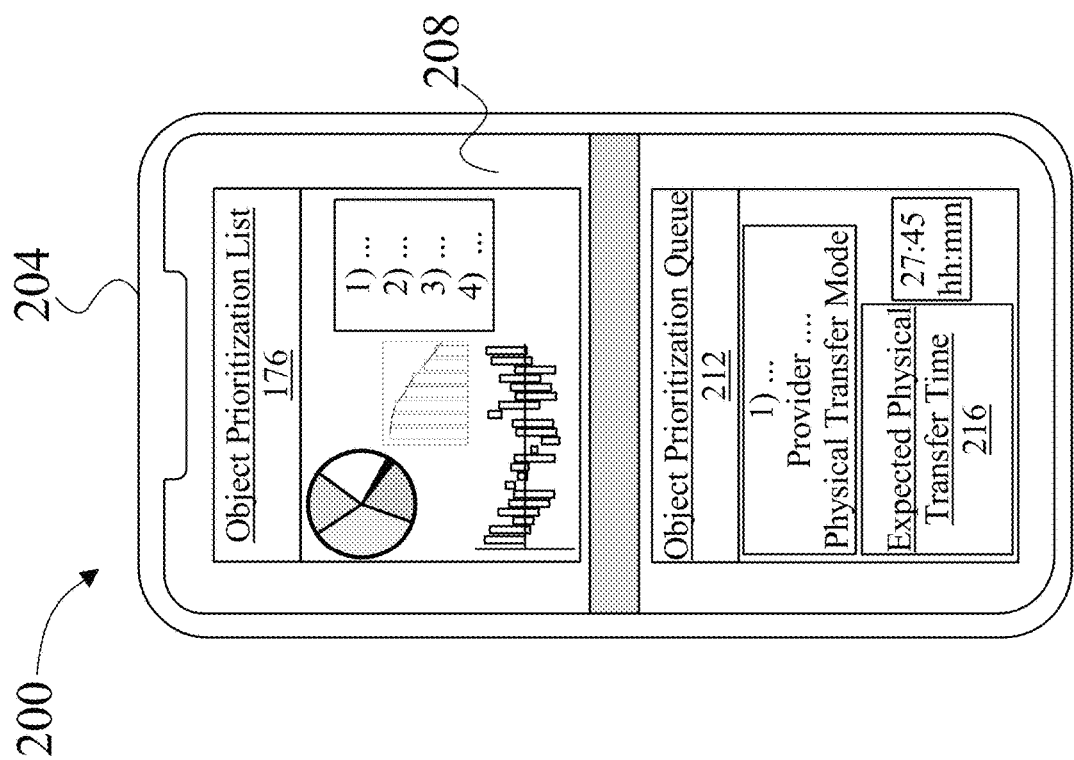
FIG. 2 is a diagrammatic representation of a non-limiting exemplary embodiment of a computing device generating a representation via a graphical user interface.

Referring now to FIG. 2, a non-limiting exemplary embodiment 200 of computing device 104 generating a representation via a graphical user interface of the object prioritization list 176. Computing device 104 may include a user device 204 such as a "smartphone", laptop, tablet, internet-of-things (JOT) integrated device, heads-up display, or the like, that a user may use for access to a graphical user interface. A "graphical user interface," as used in this disclosure, is any form of a user interface that allows a user to interface with an electronic device through graphical icons, audio indicators, text-based interface, typed command labels, text navigation, and the like, wherein the interface is configured to provide information to the user and accept input from the user. Graphical user interface 208 may accept a user input, wherein user input may include communicating with system 100 to initiate object prioritized ordering of at least an object. User input via a graphical user interface may include deselecting elements in the object prioritization list 176, scheduling the ordering of objects, viewing urgency metrics 112, utility metrics 144, reliability metrics 160, and/or any other determinations described herein. Persons skill in the art, upon review of this disclosure in its entirety, will be aware of the various ways in which a graphical user interface may display the information herein and the various devices which may be a user device.

Still referring to FIG. 2, generating the representation via a graphical user interface of the object prioritization list 176 may include an object prioritization queue and a provider for each object. An "object prioritization queue," as used in this disclosure is a collection of objects that are maintained and displayed to a user in a sequence and can be modified by the addition of objects and removal of objects that are configured for direct ordering. Object prioritization queue 212 may provide to a user the objects prioritized as described herein for a user to select as a function of affordability, etc. User may modify object prioritization queue 212 by removing objects and/or by adding objects to the queue. User may select any object in the object prioritization list 176 to communicate to system 100 to initiate ordering. Initiation of ordering may be performed by accessing financial transaction information of a user and/or prompting a user to include financial transaction information, such as credit card information. Initiation of ordering may be performed by hyperlinking the objects in the object prioritization queue, wherein "hyperlinking" is linking a word, phrase, or image, so that selection via the graphical user interface 208 sends a reference to data that the user can follow, wherein the link takes a user to a provider website, etc. Persons skill in the art, upon review of this disclosure in its entirety, will be aware of the various ways in which the graphical user interface may display the object prioritization queue and the various ways in which the user may initiate ordering of an object.

Continuing in reference to FIG. 2, generating the representation via a graphical user interface of the object prioritization list 176 may include a physical transfer mode 148 for each object and an expected physical transfer time. An "expected physical transfer time," as used in this disclosure, is an expected physical transfer time determined by computing device 104 according to the calculations described herein. An expected physical transfer time 216 may be provided to a user as a timer, countdown, posted time, and the like. Graphical user interface displaying the object prioritization list 176 may include a physical transfer mode 148 for each object in the object prioritization queue 212.

Figure 3:
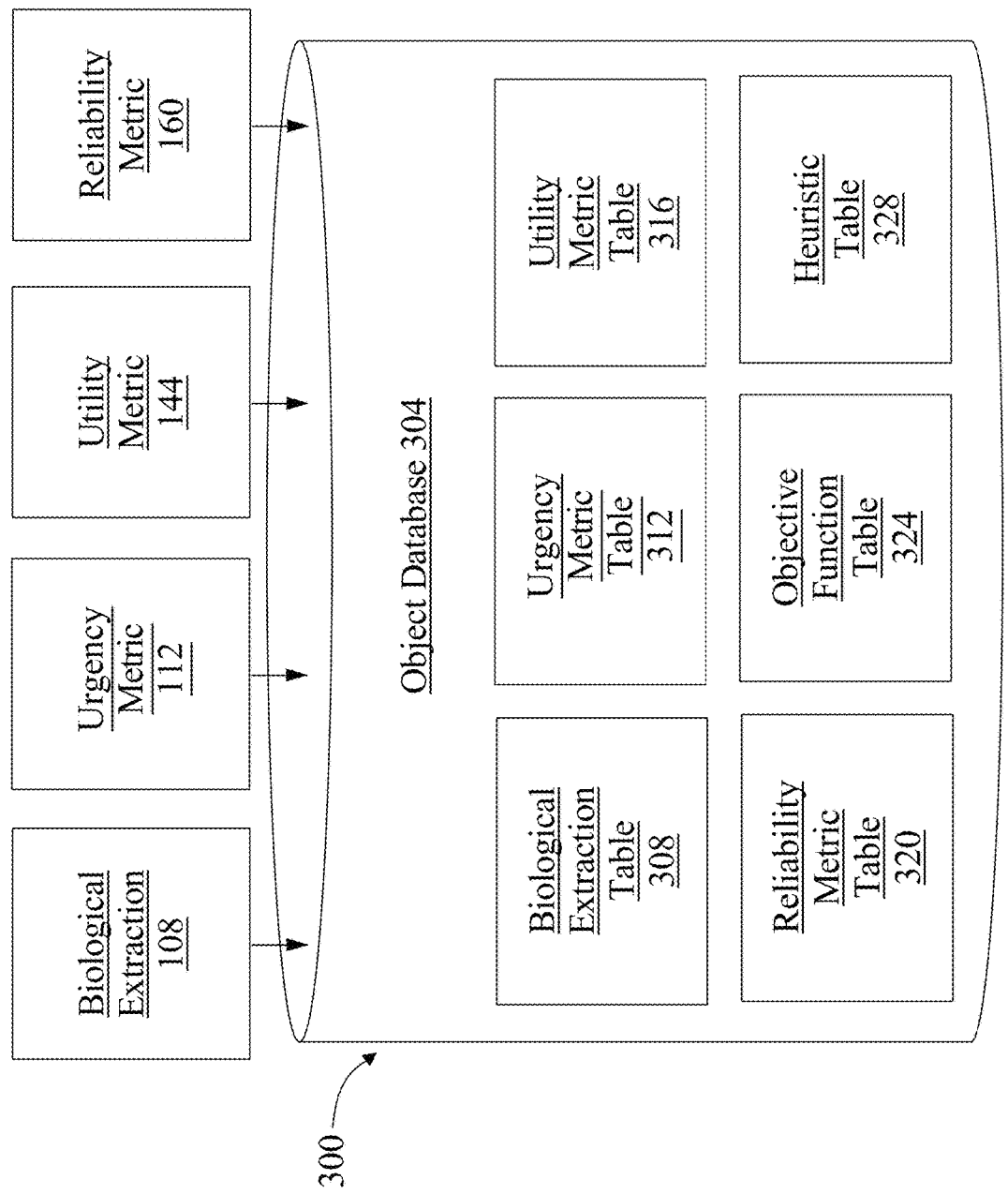
FIG. 3 is a block diagram of a non-limiting exemplary embodiment of an object database.

Referring now to FIG. 3, a non-limiting exemplary embodiment 300 of an object database 304 is illustrated. Object database 304 may be implemented, without limitation, as a relational database, a key-value retrieval database such as a NOSQL database, or any other format or structure for use as a database that a person skilled in the art would recognize as suitable upon review of the entirety of this disclosure. Object database 304 may alternatively or additionally be implemented using a distributed data storage protocol and/or data structure, such as a distributed hash table and the like. Object database 304 may include a plurality of data entries and/or records, as described above. Data entries in an object database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 3, object database 304 may include, without limitation, a biological extraction table 308, urgency metric table 312, utility metric table 316, reliability metric table 320, objective function table 324, and/or heuristic table 328. Determinations by a machine-learning process, machine-learning model, ranking function, mapping algorithm and/or objection function, may also be stored and/or retrieved from the object database 304, for instance in non-limiting examples a classifier describing a plurality of biological extraction 108 as it relates to a plurality of objects, wherein a classifier is an identifier that denotes a subset of data that contains a heuristic and/or relationship, as may be useful to system 100 described herein. As a non-limiting example, object database 304 may organize data according to one or more instruction tables. One or more object database 304 tables may be linked to one another by, for instance in a non-limiting example, common column values. For instance, a common column between two tables of object database 304 may include an identifier of a submission, such as a form entry, textual submission, global position system (GPS) coordinates, addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of an object database 304 may include, as a non-limiting example, a biological extraction table 308, which may include categorized biological extraction 108 data, as described above, including biological, physiological, chemical, genetic, medical histories, diseases, etc., data. One or more tables may include urgency metric table 312, which may include a urgency metrics 112, machine-learning models used to generate urgency metrics, classifiers, data, and the like, for instance and without limitation, that system 100 may use to retrieve and/or store urgency metrics, associated with user. One or more tables may include utility metric table 316, which may include a utility metrics 144, including classifiers, data, and the like, for instance and without limitation, that system 100 may use to retrieve and/or store utility metrics 144, associated with user. One or more tables may include reliability metric table 320, which may include reliability metrics 160, including, classifiers, data, and the like, for instance and without limitation, that system 100 may use to retrieve and/or store reliability metrics 160, associated with user. One of more tables may include an objective function table 324, which may include a plurality of constraints 188 and/or past objective function outputs, determinations, variables, and the like, organized into subsets of data. One or more tables may include, without limitation, a heuristic table 328, which may organize orderings, scores, models, outcomes, functions, numerical values, vectors, matrices, and the like, that represent determinations, optimizations, iterations, variables, and the like, include one or more inputs describing potential mathematical relationships, as described herein.

Figure 4:
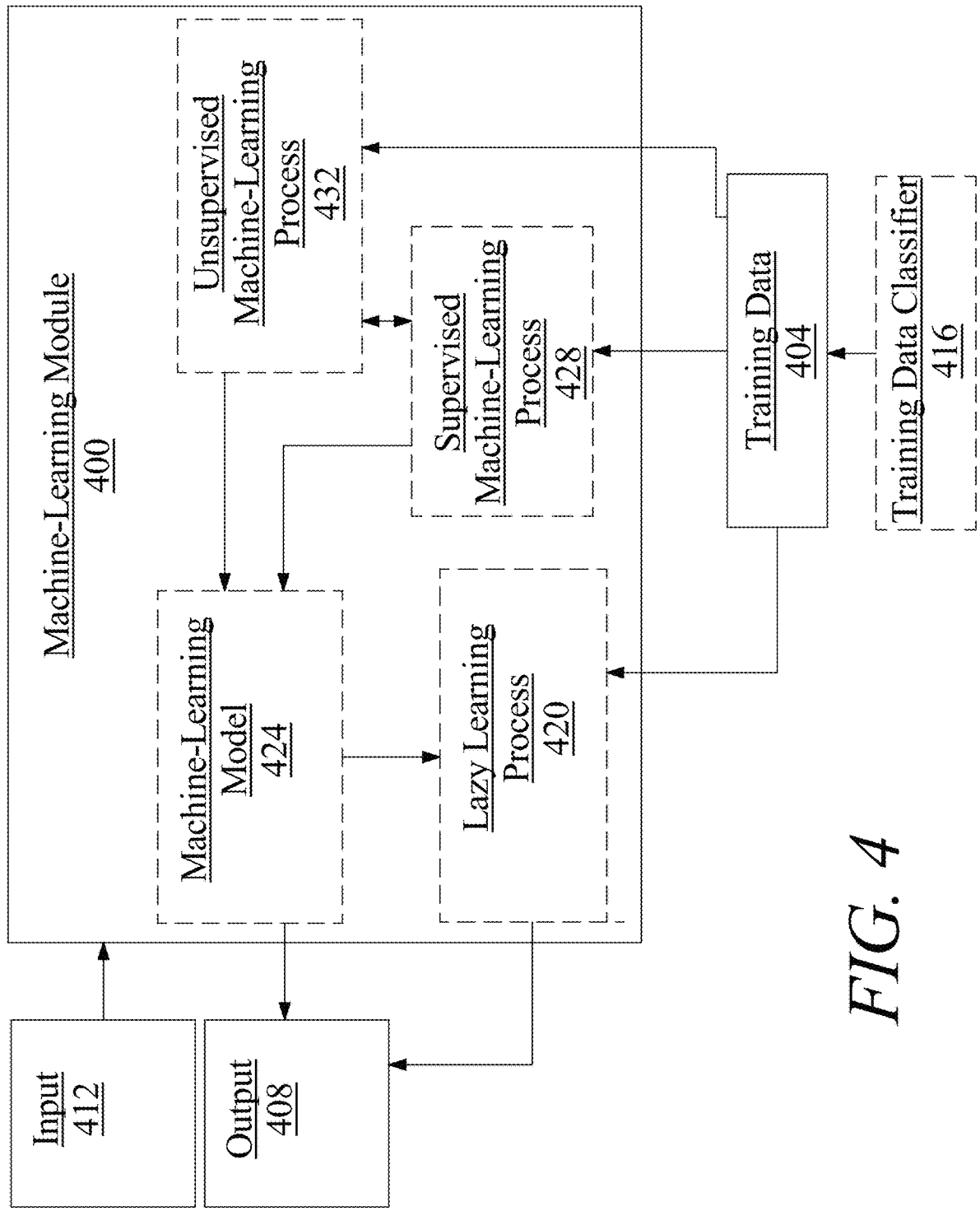
FIG. 4 is a block diagram of a non-limiting exemplary embodiment of a machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail herein. Training data 404 used by machine-learning module 400 may correlate any input data as described in this disclosure to any output data as described in this disclosure.

Further referring to FIG. 4, training data may be filtered, sorted, and/or selected using one or more supervised and/or unsupervised machine-learning processes and/or models as described in further detail herein; such models may include without limitation a training data classifier 416. Training data classifier 416 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a process whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to elements that characterizes a sub-population, such as a subset of physical transfer paths, physical transfer modes, and/or other analyzed items and/or phenomena for which a subset of training data may be selected.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include an ordering of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a plurality of first simulated alimentary elements 124 and biological extraction 108 as described above as inputs, candidate second simulated alimentary elements 128 as outputs, and a ranking function representing a desired form of relationship to be detected between inputs and outputs; ranking function may, for instance, seek to maximize the probability that a given input and/or combination of elements inputs is associated with a given output to minimize the probability that a given input is not associated with a given output. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 4, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 404.

Figure 5:
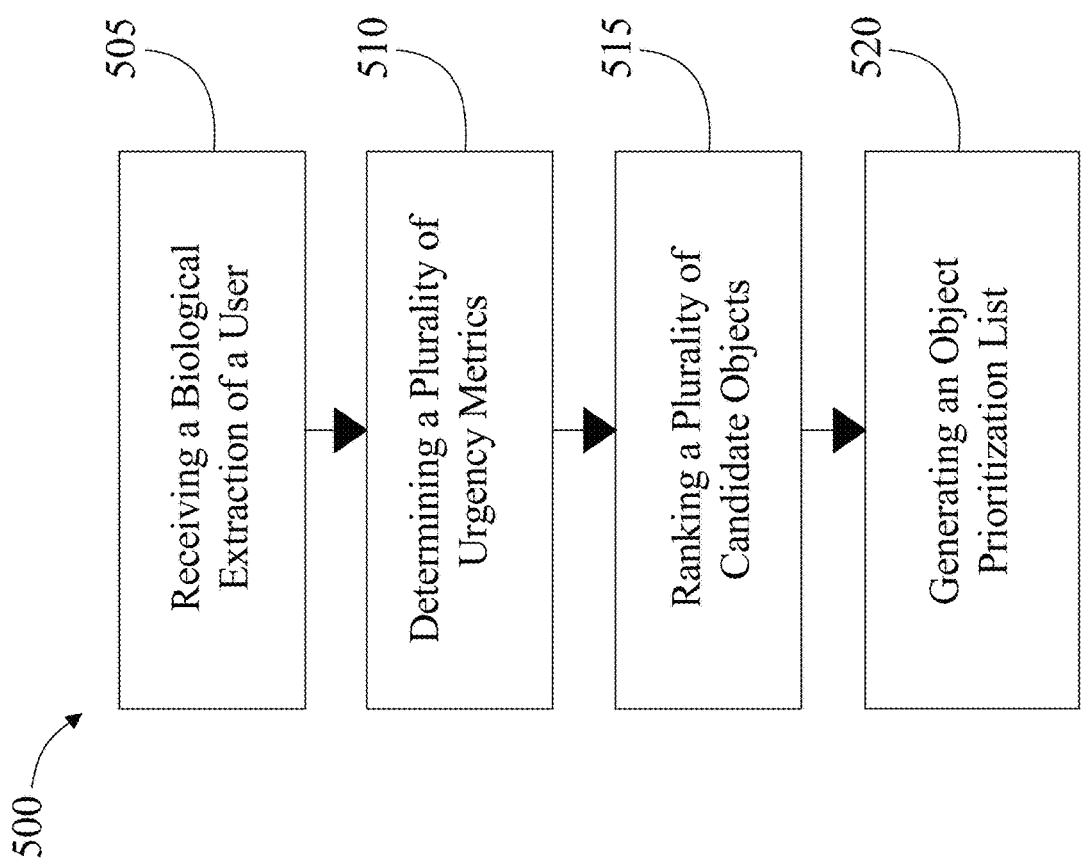
FIG. 5 is a block diagram of an exemplary workflow of a method for generating an object prioritization list for physical transfer.

Referring now to FIG. 5, an exemplary embodiment of a method 500 for generating an object prioritization list for physical transfer is illustrated. At step 505, computing device 104 is configured for receiving a biological extraction 108 of a user; this may be implemented, without limitation, as described above in reference to FIGS. 1-4.

Still referring to FIG. 5, at step 510, computing device 104 is configured for determining, using the biological extraction 108, a plurality of urgency metrics 112 wherein determining the plurality of urgency metrics 112 includes training a urgency machine-learning model 116 with training data that includes a plurality of entries wherein each entry relates user biological extraction to metrics of urgency correlated to object-addressable maladies, and determining the plurality of urgency metrics 112 as a function of the urgency machine-learning model 116; this may be implemented, without limitation, as described above in reference to FIGS. 1-4.

Continuing in reference to FIG. 5, at step 515, computing device 104 is configured for ordering, using a first ranking machine-learning process 120, a plurality of candidate objects 128 as a function of the plurality of urgency metrics 112. Ordering a plurality of candidate objects 128 as a function of the plurality of urgency metrics 112 includes identifying, using the plurality of urgency metrics 112 and a constituent machine-learning process 124, a plurality of candidate objects 128; this may be implemented, without limitation, as described above in reference to FIGS. 1-4.

Continuing in reference to FIG. 5, at step 520, computing device 104 is configured for generating, using the computing device, an object prioritization list 176, wherein generating the object prioritization list 176 includes using a prioritization machine-learning process 184 to generate a plurality of candidate object prioritizations 180. Generating the object prioritization list 176 may include querying a plurality of providers for the plurality of candidate objects, wherein retrieving may include generating a plurality of provider identifiers for the plurality of providers and generating, using the plurality of provider identifiers, a plurality of utility metrics 144 for the plurality of objects. Generating the object prioritization list 176 may include searching for a plurality of physical transfer modes for the plurality of objects and filtering as a function of the plurality of physical transfer modes. Generating the object prioritization list 176 may include generating a plurality of reliability metrics 160 for each combination of the plurality of physical transfer models with each of the plurality of objects. Generating the object prioritization list 176 may include using a third ranking machine-learning process 164 to generate a utility ordering 168 of the plurality of physical transfer modes as a function of the plurality of reliability metrics 160 and the plurality of urgency ordering 152. Generating the object prioritization list 176 using a prioritization machine-learning process 184 may include generating an objective function 192 of the plurality of candidate object prioritizations 180 as a function of a plurality of constraints 188, wherein minimizing the objective function 192 minimizes the time of physical transfer of the plurality of objects as a function of object priority. Computing device 104 may select the object prioritization list 176 that minimizes the time of physical transfer of the plurality of objects as a function of object priority. The object prioritization list 176 may include generating a representation of an object prioritization queue and a provider for each object the via a graphical user interface. Generating the representation via the graphical user interface of the object prioritization list 176 may include a physical transfer mode for each object and a physical transfer time; this may be implemented, without limitation, as described above in reference to FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
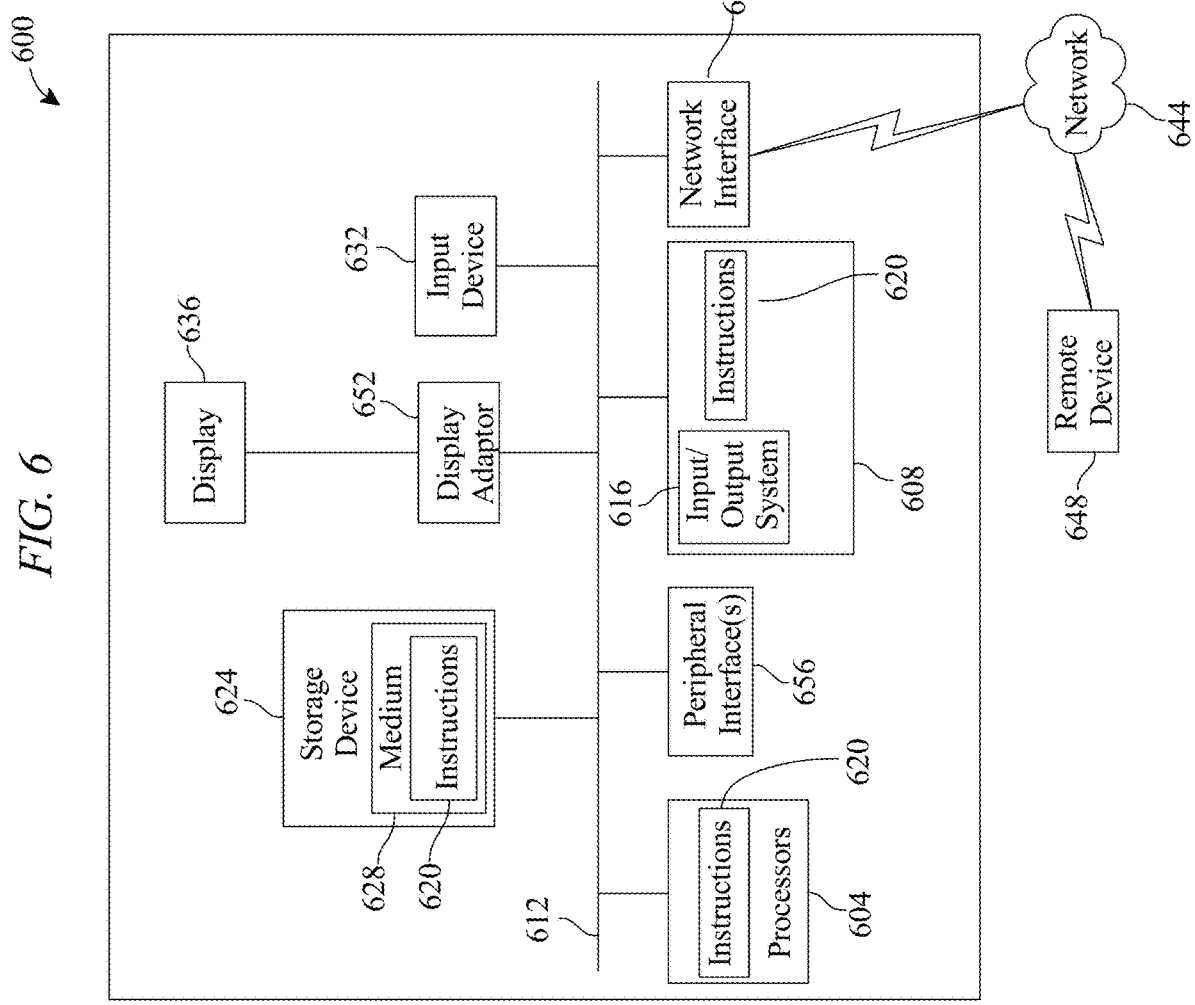
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an object prioritization list for physical transfer, the system comprising:
    a computing device, wherein the computing device is further configured to:
        receive a biological extraction of a user;
        identify at least a co-morbidity datum as a function of the biological extraction;
        determine, using the biological extraction and the at least a co-morbidity datum, a plurality of urgency metrics, wherein determining the plurality of urgency metrics further comprises:
            training an urgency machine-learning model with training data that includes a plurality of entries wherein each entry correlates biological extraction data to metrics of urgency of object-addressable maladies; and
            determining the plurality of urgency metrics as a function of the urgency machine-learning model;
        order, using a first ranking machine-learning process, a plurality of candidate objects as a function of the plurality of urgency metrics; and
        generate an object prioritization list as a function of a prioritization machine-learning model, wherein the prioritization machine-learning model inputs a utility ordering of the plurality of candidate objects and outputs the plurality of candidate objects in a prioritized ordering, wherein generating the object prioritization list further comprises:
            querying a plurality of providers for the plurality of candidate objects, wherein retrieving further comprises generating a plurality of provider identifiers for the plurality of providers;
            generating, using the plurality of provider identifiers, a plurality of utility metrics for the plurality of candidate objects, wherein each utility metric indicates a value of a benefit associated with a candidate object of the plurality of candidate objects and expediting a physical transfer of each candidate object of the plurality of candidate objects;
            searching for a plurality of physical transfer modes for the plurality of candidate objects;
            generating a plurality of reliability metrics for each mode of the plurality of physical transfer modes with each of the plurality of candidate objects; and
            generating a representation of an object prioritization queue and a provider for each object via a graphical user interface (GUI), wherein generating the representation of an object prioritization queue comprises hyperlinking each object in the object prioritization queue.

2. The system of claim 1, wherein ordering the plurality of candidate objects further comprises identifying, using the plurality of urgency metrics and a constituent machine-learning process, a plurality of candidate objects.

3. The system of claim 1, wherein generating the object prioritization list further comprises:
    filtering as a function of the plurality of physical transfer modes.

4. The system of claim 1, wherein generating the object prioritization list further comprises using a third ranking machine-learning process to generate a utility ordering of the plurality of physical transfer modes as a function of the plurality of reliability metrics and the plurality of urgency ordering.

5. The system of claim 1, wherein generating the object prioritization list using a prioritization machine-learning process further comprises:
    generating an objective function of the plurality of candidate object prioritizations as a function of a plurality of constraints, wherein minimizing the objective function minimizes the time of physical transfer of the plurality of candidate objects as a function of object priority.

6. The system of claim 5, wherein the computing device selects the object prioritization list that minimizes the time of physical transfer of the plurality of candidate objects as a function of object priority.

7. The system of claim 1, wherein generating the representation via the graphical user interface of the object prioritization list includes a physical transfer mode for each object and a physical transfer time.

8. A method for generating an object prioritization list for physical transfer, the method comprising:
    receiving, by a computing device, a biological extraction of a user;
    identifying, by the computing device, at least a co-morbidity datum as a function of the biological extraction;
    determining, by the computing device, using the biological extraction and the at least a co-morbidity datum, a plurality of urgency metrics, wherein determining the plurality of urgency metrics further comprises:
   training an urgency machine-learning model with training data that includes a plurality of entries wherein each entry correlates biological extraction data to metrics of urgency of object-addressable maladies; and
   determining the plurality of urgency metrics as a function of the urgency machine-learning model;
ordering, by the computing device, using a first ranking machine-learning process, a plurality of candidate objects as a function of the plurality of urgency metrics; and
generating, by the computing device, an object prioritization list as a function of a prioritization machine-learning model, wherein the prioritization machine-learning model inputs a utility ordering of the plurality of candidate objects and outputs the plurality of candidate objects in a prioritized ordering, wherein generating the object prioritization list further comprises:
   querying a plurality of providers for the plurality of candidate objects, wherein retrieving further comprises generating a plurality of provider identifiers for the plurality of providers;
   generating, using the plurality of provider identifiers, a plurality of utility metrics for the plurality of candidate objects, wherein each utility metric indicates a value of a benefit associated with a candidate object of the plurality of candidate objects and expediting a physical transfer of each candidate object of the plurality of candidate objects;
   searching for a plurality of physical transfer modes for the plurality of candidate objects;
   generating a plurality of reliability metrics for each mode of the plurality of physical transfer modes with each of the plurality of candidate objects; and
   generating a representation of an object prioritization queue and a provider for each object via a graphical user interface (GUI), wherein generating the representation of an object prioritization queue comprises hyperlinking each object in the object prioritization queue.

9. The method of claim 8, wherein ordering the plurality of candidate objects further comprises identifying, using the plurality of urgency metrics and a constituent machine-learning process, a plurality of candidate objects.

10. The method of claim 8, wherein generating the object prioritization list further comprises:
   filtering as a function of the plurality of physical transfer modes.

11. The method of claim 8, wherein generating the object prioritization list further comprises using a third ranking machine-learning process to generate a utility ordering of the plurality of physical transfer modes as a function of the plurality of reliability metrics and the plurality of urgency ordering.

12. The method of claim 8, wherein generating the object prioritization list using a prioritization machine-learning process further comprises:
   generating an objective function of the plurality of candidate object prioritizations as a function of a plurality of constraints, wherein minimizing the objective function minimizes the time of physical transfer of the plurality of candidate objects as a function of object priority.

13. The method of claim 12, wherein the computing device selects the object prioritization list that minimizes the time of physical transfer of the plurality of candidate objects as a function of object priority.

14. The method of claim 8, wherein generating the representation via the graphical user interface of the object prioritization list includes a physical transfer mode for each object and a physical transfer time.

15. The system of claim 1, wherein hyperlinking further comprises linking a phrase to each object in the object prioritization queue, wherein a selection via the GUI causes the user to be directed to a provider website.

16. The method of claim 8, wherein hyperlinking further comprises linking a phrase to each object in the object prioritization queue, wherein a selection via the GUI causes the user to be directed to a provider website.

* * * * *